United States Patent
Candidus et al.

(10) Patent No.: US 10,349,866 B2
(45) Date of Patent: Jul. 16, 2019

(54) STRAP-FASTENING APPARATUS AND PATIENT SUPPORT APPARATUS WITH A STRAP-FASTENING APPARATUS

(71) Applicants: Yvonne Candidus, Fürth (DE); Daniel Driemel, Oederan (DE); Wolfgang Kraus, Fürth (DE); Thomas Kundner, Buckenhof (DE); Martin Zigann, Möhrendorf (DE); Stephan Zink, Erlangen (DE)

(72) Inventors: Yvonne Candidus, Fürth (DE); Daniel Driemel, Oederan (DE); Wolfgang Kraus, Fürth (DE); Thomas Kundner, Buckenhof (DE); Martin Zigann, Möhrendorf (DE); Stephan Zink, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 874 days.

(21) Appl. No.: 14/801,975

(22) Filed: Jul. 17, 2015

(65) Prior Publication Data

US 2016/0022170 A1    Jan. 28, 2016

(30) Foreign Application Priority Data

Jul. 23, 2014   (DE) .................. 10 2014 214 429

(51) Int. Cl.
*A61B 6/04* (2006.01)
*A61B 5/055* (2006.01)
*A44B 11/25* (2006.01)

(52) U.S. Cl.
CPC .......... *A61B 5/0555* (2013.01); *A61B 6/0421* (2013.01); *A44B 11/2503* (2013.01)

(58) Field of Classification Search
CPC ... A61B 5/0555; A61B 6/0421; A61B 6/0407; A44B 11/2503; A44B 11/005; A44B 11/2534; A61F 5/3769; A61F 5/3776; B60R 2022/028; A61G 13/101; A61G 13/12; A61G 13/1205; A61G 13/122; A61G 1/044

(Continued)

(56) References Cited

U.S. PATENT DOCUMENTS 5,113,876 A * 5/1992 Herman .............. A61F 5/05883
                                                                24/702
5,433,222 A   7/1995 Boomgaarden et al.

(Continued)

FOREIGN PATENT DOCUMENTS

DE   102004016330 B3   7/2005

OTHER PUBLICATIONS

German Office Action for related German Application No. 10 2014 214 429.9, dated Mar. 10, 2015, with English Translation.

*Primary Examiner* — Kari K Rodriquez
*Assistant Examiner* — Camtu T Nguyen
(74) *Attorney, Agent, or Firm* — Lempia Summerfield Katz LLC

(57) ABSTRACT

A strap-fastening apparatus for fastening safety straps is provided, wherein the strap-fastening apparatus has at least one fastening rail and at least one fastening clip. The at least one fastening clip has a strap-fastening element and the strap-fastening element, in a state of the at least one fastening clip arranged with the at least one fastening rail, is arranged within the at least one fastening rail.

17 Claims, 5 Drawing Sheets

(58) Field of Classification Search
USPC .............................................. 5/601
See application file for complete search history.

(56) References Cited

U.S. PATENT DOCUMENTS 8,302,610 B1 * 11/2012 Larson ................. A61F 5/37
128/870
2008/0186027 A1 8/2008 Kassai

* cited by examiner

STRAP-FASTENING APPARATUS AND PATIENT SUPPORT APPARATUS WITH A STRAP-FASTENING APPARATUS

CROSS-REFERENCE TO RELATED APPLICATIONS

This application claims the benefit of DE 10 2014 214 429.9, filed on Jul. 23, 2014, which is hereby incorporated by reference in its entirety.

TECHNICAL FIELD

The present embodiments relate to a strap-fastening apparatus for fastening safety straps for, in particular, a medical imaging examination, wherein the strap-fastening apparatus has at least one fastening rail and at least one fastening clip.

BACKGROUND

For a medical imaging examination using a medical imaging apparatus on a patient, the patient is positioned on a patient support apparatus and is introduced into a patient examination region of the medical imaging apparatus together with a couch of the patient support apparatus. In order to protect the patient, the patient is secured on the patient couch by safety straps. Moreover, medical accessory units that are required for the medical imaging examination are also secured together with the patient using the safety straps. These medical accessory units may include for instance local coil units for a medical magnetic resonance examination and/or an EKG unit, etc. These safety straps may be fastened and/or fixed on or to the patient support apparatus.

SUMMARY AND DESCRIPTION

The scope of the present invention is defined solely by the appended claims and is not affected to any degree by the statements within this summary. The present embodiments may obviate one or more of the drawbacks or limitations in the related art.

The object in particular is to provide a strap-fastening apparatus, with which a simple and secure fastening and/or fixing of safety straps is enabled for a medical imaging examination.

The embodiments are based on a strap-fastening apparatus for fastening safety straps, wherein the strap-fastening apparatus has at least one fastening rail and at least one fastening clip.

It is proposed that the at least one fastening clip has a strap-fastening element and the strap-fastening element, in a state of the at least one fastening clip arranged with the at least one fastening rail, is arranged within the at least one fastening rail.

The strap-fastening apparatus may be configured for fastening objects, (e.g., a patient and/or additional units), to a patient support apparatus, in particular, a couch of the patient support apparatus. The strap-fastening apparatus may be configured for medical imaging examinations on the patient using medical imaging apparatuses. The strap-fastening apparatus may also be included in the patient support apparatus. For instance, the fastening rail may be arranged here within a couch of the patient support apparatus. Alternatively, or in addition, the strap-fastening apparatus may also include at least partially accessory units. For instance, the at least one fastening rail and/or the at least one fastening clip may be included in a local magnetic resonance coil apparatus.

The at least one fastening clip and the at least one fastening rail may be formed of elements that correspond to one another, so that in order to fasten a safety strap, the safety strap is arranged on the least one fastening clip and the at least one fastening clip may be fastened within the at least one fastening rail. An arrangement, e.g., a fastening and/or fixing of the at least one fastening clip within the at least one fastening rail, takes place exclusively by the at least one fastening rail and the fastening clip corresponding to the at least one fastening rail so that no further units and/or components are necessary herefor.

In this context, "arranged within the fastening rail" may refer to a strap-fastening element that is arranged at least 70% within the fastening rail or at least 85% within the fastening rail. The strap-fastening element may be advantageously arranged completely within the fastening rail so that the strap-fastening element does not protrude out of the fastening rail in the state of the fastening clip arranged with the fastening rail.

The strap-fastening apparatus advantageously achieves increased patient comfort since hindrance of the patient on account of the strap-fastening element may at least be reduced or even prevented by comparison with conventional strap-fastening apparatuses. Furthermore, a particularly space-saving and compact arrangement of the strap-fastening apparatus may herewith be achieved. In addition, the strap-fastening element and also an arrangement of a safety strap on the strap-fastening element may in this way also be advantageously protected against undesired adverse effects and/or damage.

It is further proposed that the at least one fastening clip has a base element on which the strap-fastening element is arranged. Aside from high stability for the strap-fastening element, an advantageous protection of the arrangement of the safety strap may be achieved in this way.

The base element, in a state of the at least one fastening clip arranged with the at least one fastening rail, may be likewise arranged at least 70% within the at least one fastening rail. The base element may be arranged at least 80% within the fastening rail or at least 85% within the fastening rail. In certain embodiments, the base element is advantageously arranged at least 90% within the fastening rail so that the strap-fastening element does not protrude from the fastening rail. This embodiment provides advantageous protection for the base element so that in a state of the fastening clip arranged on the fastening rail, damage to the base unit may be advantageously prevented. Moreover, increased comfort for the patient may also be provided since hindrance of the patient on account of the strap-fastening apparatus may at least be reduced and/or prevented.

Particularly high stability of the at least one fastening clip may be advantageously achieved if the base element is embodied in a U-shape with two limb elements and the strap-fastening element is arranged between the two limb elements. The strap-fastening element may be arranged here with a first end region on a first or the two limb elements and with a second end region on a second of the two limb elements. The strap-fastening element may be embodied in the form of a web, so that a safety strap of the strap-fastening apparatus may be guided around the strap-fastening element.

In an advantageous development, it is proposed that the at least one fastening clip has an actuation element. A simple actuation, (e.g., release of the at least one fastening clip from the fastening rail and/or a fixing of the at least one fastening clip within the fastening rail), may be advantageously achieved for medical operating staff. The medical operating staff may exert a force via the actuation element on the fastening clip, for instance, to move the fastening clip within the fastening rail and/or to release the fastening clip in a state arranged with the fastening rail from the fastening rail. The actuation element may be arranged within the fastening clip such that the actuation element, in an arranged state of the fastening clip with the fastening rail, protrudes from the fastening rail and a simple and safe actuation may take place in this way by medical operating staff.

It is further proposed that the at least one fastening clip includes a securing element. An advantageous securing of the position of the at least one fastening clip may herewith be achieved within the at least one fastening rail of the strap-fastening apparatus. The securing element particularly advantageously includes a snap-on element, so that a constructively simple and time-saving securing of the position of the at least one fastening clip may be achieved within the fastening rail.

In a further embodiment, the at least one fastening clip has a connecting web for connecting the actuation element with the base element, wherein the securing element is arranged on the connecting web. An advantageous arrangement of the securing element, (e.g., a snap-on element), may herewith be achieved by the securing element being arranged on a region of the fastening clip embodied as a spring element. The region embodied as a spring element, (e.g., the connecting web), is embodied here such that in order to release the fastening clip from the fastening rail, pressure is exerted onto the fastening clip, (e.g., onto the actuation element), and this pressure results in a deformation of the connecting web. After the pressure on the fastening clip is released, the connecting web once again assumes its original shape. This embodiment enables a particularly simple release of a fastening position and/or a state of the at least one fastening clip arranged with the at least one fastening rail for the medical operating staff.

The at least one fastening rail particularly advantageously has an opening and a maximum width, wherein a width of the opening amounts to at least 60% of the maximum width. The width of the opening may be at least 75% of the maximum width or at least 80% of the maximum width. This embodiment allows a particularly simple introduction of the at least one fastening clip into the at least one fastening rail. A particularly simple cleaning of the at least one fastening rail may also be advantageously achieved on account of the large opening.

In a further embodiment, it is proposed that the at least one fastening rail has a longitudinal extent and the opening has a uniform width in the direction of this longitudinal extent. A particularly simple and safe introduction of the fastening clip into the at least one fastening rail may herewith be achieved. The introduction of the fastening clip at any point on the at least one fastening rail may in particular take place and in this way a work flow for a medical operating personnel may be advantageously simplified. Moreover, a particularly cost-effective and easily producible fastening rail may herewith be provided.

In a further embodiment, the at least one fastening rail has a web-type rail element, which is arranged in an opening region of the at least one fastening rail, wherein the web-type rail element is only arranged on an edge region running in the longitudinal extent of the at least one fastening rail. A particularly simple cleaning of the fastening rail may herewith be achieved, since a concealed region, in particular a region concealed by the web-type rail element, is present within the fastening rail only on one side of the fastening rail. Furthermore, the fastening clip may be secured against falling out of the fastening rail, (e.g., during a positioning of the fastening clip within the fastening rail), by the web-type rail element. A second edge region, which likewise runs in the longitudinal extent of the at least one fastening rail and faces the edge region with the web-type rail element within the at least one fastening rail, may be formed by a straight continuation of a receiving region of the at least one fastening rail.

In a further embodiment, it is proposed that the at least one fastening clip, in a state in which the at least one fastening clip has a snap-on connection with the at least one fastening rail, is arranged so as to be movable within the at least one fastening rail in a direction of a longitudinal extent of the at least one fastening rail. A simple and precise positioning of the fastening clip in the direction of the longitudinal extent of the fastening rail within the fastening rail may be achieved and a particularly simple and precise positioning of a securing strap is thus enabled since only the position of the fastening clip in the longitudinal extent of the fastening rail has to be defined. In the state in which the at least one fastening clip has a snap-on connection with the at least one fastening rail, the at least one fastening clip is secured from falling out of the at least one fastening rail during a positioning in the longitudinal extent of the at least one fastening rail by the fastening element of the at least one fastening clip and by the web-type rail element.

It is further proposed that the at least one fastening clip locks with the at least one fastening rail upon the effect of a tensile force on the strap-fastening element. The fastening clip may herewith be locked within the fastening rail particularly easily by medical operating staff tightening the safety strap. Locking the fastening clip with the fastening rail may take place by canting the fastening clip within the fastening rail, so that a movement of the fastening clip in the direction of the longitudinal extent of the fastening rail is prevented.

In an advantageous development, a force perpendicular to the longitudinal extent of the at least one fastening rail acts on the at least one fastening clip to release a lock between the at least one fastening clip and the at least one fastening rail. The force particularly advantageously acts here on the actuation element of the fastening clip in order to release the lock. A particularly simple release of the fastening clip from a lock with the fastening rail may be achieved in this way. The required force of the web-type rail element to the opposing edge region of the fastening rail may act to release the fastening clip. This direction particularly advantageously corresponds to the force of a direction from outside onto the patient that releases the lock so that in order to release the lock, medical operating staff do not have to grip between the patient and the strap-fastening apparatus, in particular the fastening clip. An unwanted release of the lock by the patient may moreover also be prevented in this way for instance during a medical imaging examination.

Furthermore, the embodiments are based on a patient support apparatus with a strap-fastening apparatus for fastening safety straps, wherein the strap-fastening apparatus has at least one fastening rail and at least one fastening clip, wherein the at least one fastening clip has a strap-fastening element that, in a state of the at least one fastening clip arranged with the at least one fastening rail, is arranged within the at least one fastening rail. Increased patient comfort may be advantageously achieved in this way since hindrance to the patient on account of the strap-fastening element may be prevented. Furthermore, a particularly space-saving and compact arrangement of the strap-fastening apparatus may herewith be achieved. In addition, the strap-fastening element and also an arrangement of a safety strap on the strap-fastening element may in this way be advantageously protected against undesired adverse effects and/or damage.

The advantages of the medical patient support apparatus correspond to the advantages of the medical strap-fastening apparatus, explained above in detail. Features, advantages or alternative embodiments mentioned herein are also to be applied to the other claimed subject matter and vice versa.

It is further proposed that the patient support apparatus has a couch that includes the at least one fastening rail and the at least one fastening rail is arranged in an edge region of the couch, where the edge region extends along a longitudinal extent of the couch. A particularly space-saving fastening may herewith be advantageously achieved at any position in the direction of the longitudinal extent of the couch.

It is also proposed that to release a lock between the at least one fastening clip and the at least one fastening rail, a force at right angles to the longitudinal extent of the at least one fastening rail acts inwards on the at least one fastening clip from an edge region of the couch. A particularly simple release of the at least one fastening clip may be achieved in this way. Furthermore, in order to release the lock medical operating staff do not have to grip between the patient and the strap-fastening apparatus, in particular the fastening clip, which simplifies both a workflow for the medical operating personnel and also increases patient comfort. An unwanted release of the lock by the patient may moreover also be prevented in this way, for instance during a medical imaging examination.

In a further embodiment, it is proposed that the strap-fastening apparatus is compatible with a local magnetic resonance coil apparatus. The strap-fastening apparatus may herewith be advantageously integrated into already existing systems, (e.g., magnetic resonance systems). The local magnetic resonance coil apparatuses may include for instance fixed magnetic resonance coil apparatuses, which may be arranged within the fastening rail of the strap-fastening apparatus. Furthermore, the local magnetic resonance coil apparatuses may for instance also be formed of magnetic resonance coil apparatuses that may be positioned on the patient, the magnetic resonance coil apparatus being secured by safety straps. It may also be conceivable here for the local magnetic resonance coil apparatus to have a fastening rail and/or a fastening clip.

Furthermore, the embodiments are based on a medical imaging apparatus having a patient support apparatus including a strap-fastening apparatus for fastening safety straps, wherein the strap-fastening apparatus has at least one fastening rail and at least one fastening clip, wherein the at least one fastening clip has a strap-fastening element and the strap-fastening element, in a state in which the at least one fastening clip is arranged with the at least one fastening rail, is arranged within the at least one fastening rail.

The advantages of the medical imaging apparatus correspond to the advantages of the medical patient support apparatus and the advantages of the medical strap-fastening apparatus, explained above in detail. Features, advantages, or alternative embodiments mentioned herein are also to be applied to the other claimed subject matter and vice versa.

DETAILED DESCRIPTION

Figure 1:
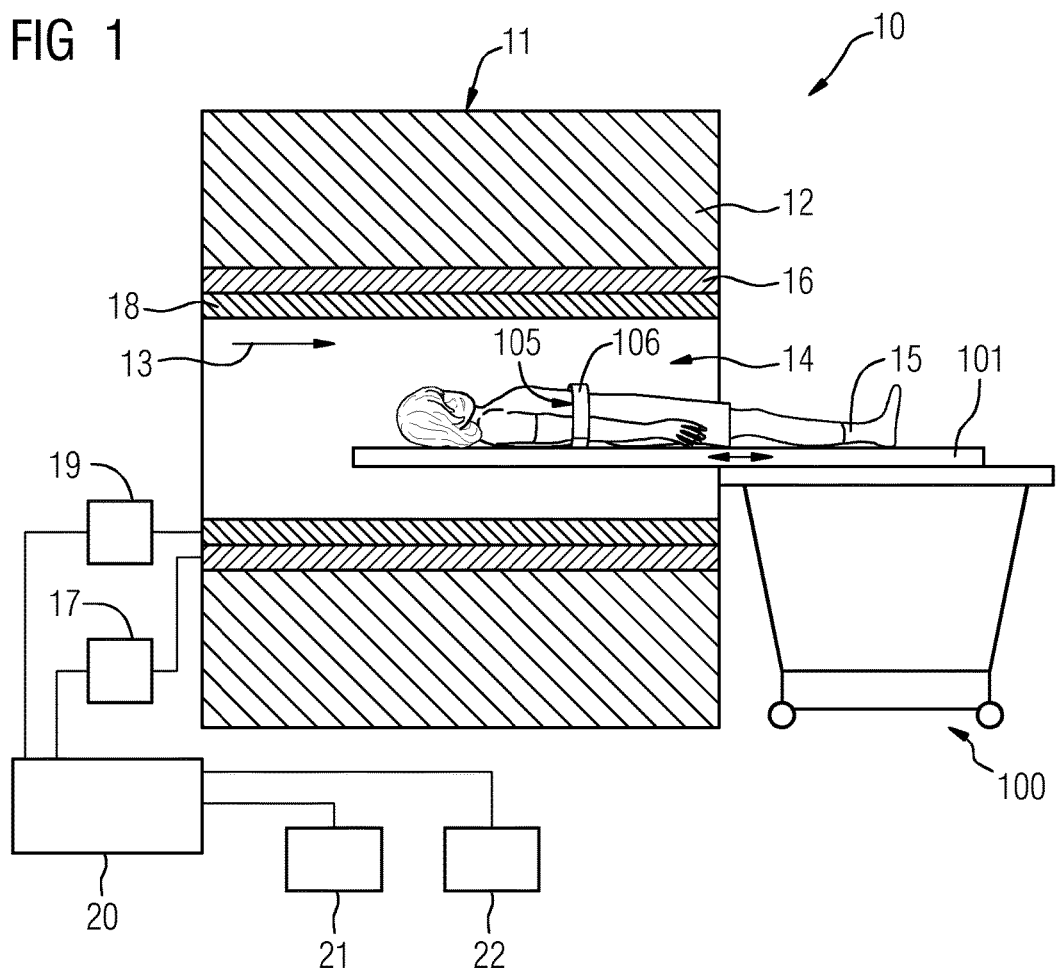
FIG. 1 depicts an example of a medical imaging apparatus in a schematic representation.

FIG. 1 depicts a medical imaging apparatus 10 schematically. In the present exemplary embodiment, the medical imaging apparatus 10 is formed by a magnetic resonance apparatus. The embodiment of the medical imaging apparatus 10 is, however, not restricted to a magnetic resonance apparatus. Instead, the medical imaging apparatus 10 may be formed by all medical imaging apparatuses that appear sensible to the person skilled in the art, like for instance a computed tomography apparatus, a positron emission tomography apparatus, etc.

The magnetic resonance apparatus includes a magnet unit 11 having a superconducting main magnet 12 for generating a powerful and in particular constant main magnetic field 13. Moreover, the magnetic resonance apparatus has a patient receiving zone 14 for receiving a patient 15. The patient receiving zone 14 is embodied in the present exemplary embodiment in a cylindrical design and is surrounded cylindrically in a peripheral direction by the magnet unit 11. An embodiment of the patient receiving zone 14 that deviates therefrom is conceivable at any time. The patient 15 may be introduced into the patient receiving zone 14 by a patient support apparatus 100 of the magnetic resonance apparatus 100. The patient positioning device 100 to this end has a couch 101 configured to be movable within the patient receiving zone 14.

The magnet unit 11 also has a gradient coil unit 16 for generating magnetic field gradients that are used for position encoding during imaging. The gradient coil unit 16 is controlled by a gradient control unit 17 of the magnetic resonance device. The magnet unit 11 furthermore has a radio frequency antenna unit 18 for exciting a polarization that becomes established in the main magnetic field 13 generated by the main magnet 12. The radio frequency antenna unit 18 is controlled by a radio frequency antenna control unit 19 of the magnetic resonance apparatus and radiates radio frequency magnetic resonance sequences into an examination space that is substantially formed by a patient receiving zone 14 of the magnetic resonance apparatus.

In order to control the main magnet 12, the gradient coil unit 17 and in order to control the radio frequency antenna control unit 19, the magnetic resonance apparatus has a system control unit 20. The control unit 20 centrally controls the magnetic resonance apparatus, such as performing a predetermined imaging gradient echo sequence for example. Moreover, the control unit 20 has an evaluation unit for evaluating image data. Control information such as imaging parameters, for example, as well as reconstructed magnetic resonance images may be displayed on a display unit 21, for example on at least one monitor, of the magnetic resonance device for viewing by an operator. Furthermore the magnetic resonance apparatus has an input unit 22 by which information and/or parameters may be input by an operator during a measurement procedure.

Figure 2:
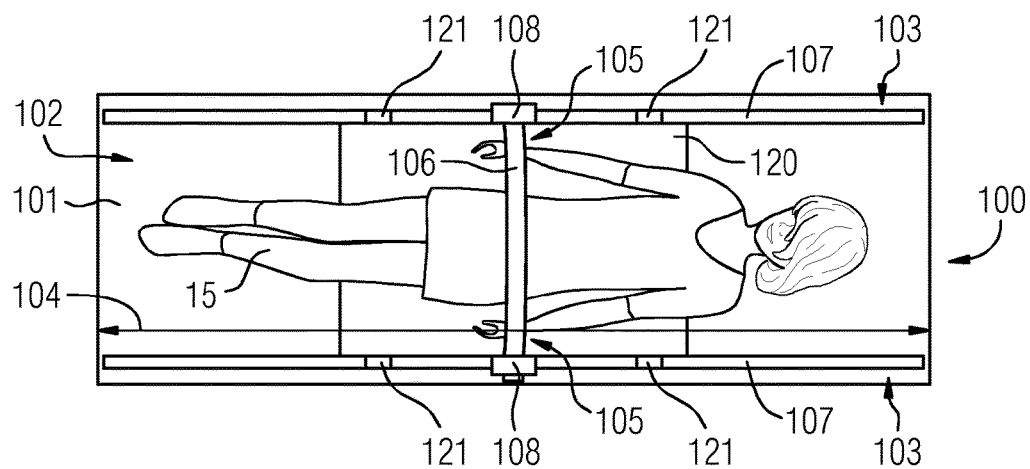
FIG. 2 depicts an example of a patient support apparatus with a strap-fastening apparatus in a schematic top view.
Figure 3:
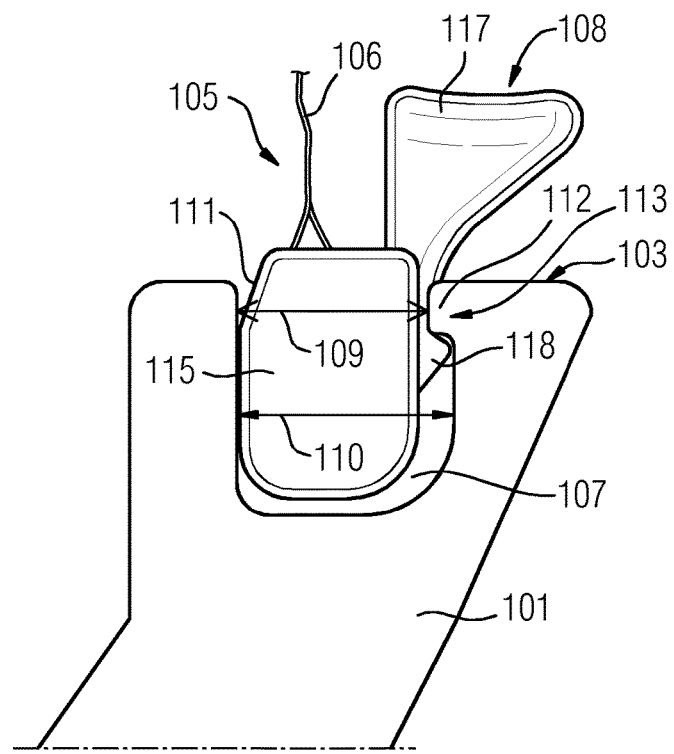
FIG. 3 depicts an example of the strap-fastening apparatus in a schematic representation.

FIG. 2 depicts a top view of the patient support apparatus 100. The patient support apparatus 100, in particular the couch 101 of the patient support apparatus 100, has a support zone 102 for supporting the patient 15. Furthermore, the couch 101 includes edge regions 103, which extend in a direction of a longitudinal extent 104 of the couch 101. The support region 102 is arranged between the two edge regions 103. The patient support apparatus 100 has a strap-fastening apparatus 105 on these edge regions 103 of the couch 101. Safety straps 106 for securing objects, in particular the patient 15 and/or additional units, are fastened to the couch 101 by the strap-fastening apparatus 105.

The strap-fastening apparatus 105 to this end has at least one fastening rail 107 and at least one fastening clip 108 (FIG. 2). In the present exemplary embodiment, the strap-fastening apparatus 105 has two fastening rails 107 and two fastening clips 108. In an alternative embodiment, the strap-fastening apparatus 105 may also include a single fastening clip 108 or more than two fastening clips 108. In an alternative embodiment, the strap-fastening apparatus may also include a single fastening rail 107 or more than two fastening rails 107.

Figure 6:
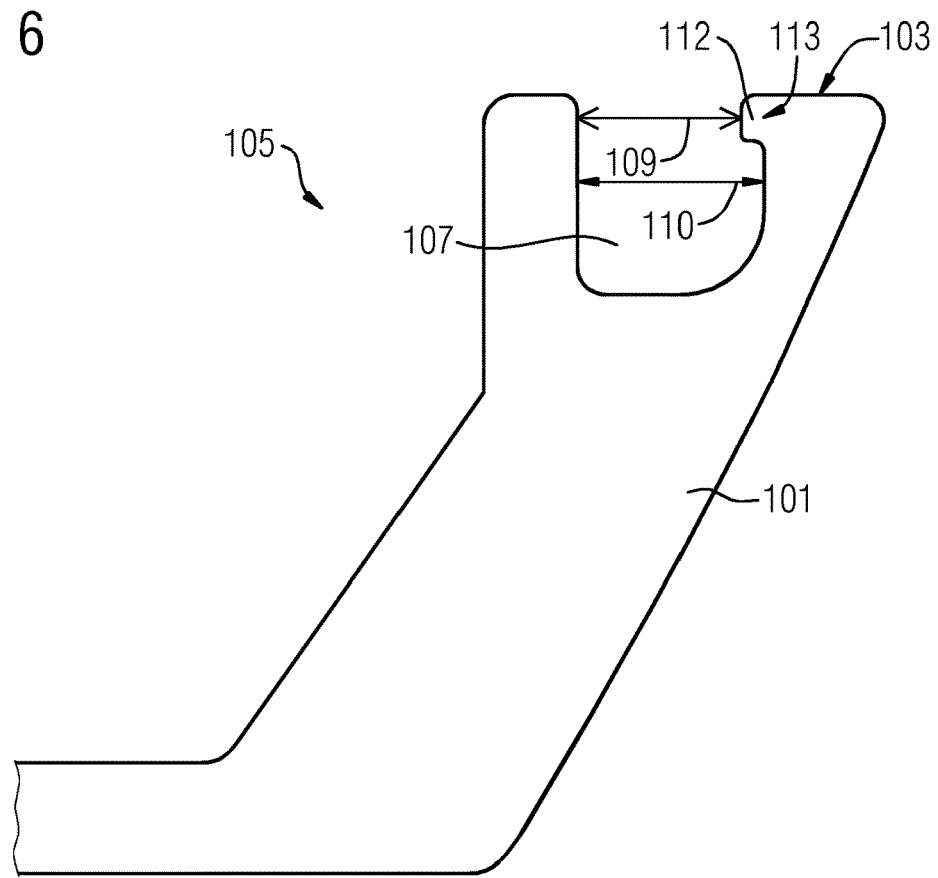
FIG. 6 depicts an example of a fastening rail of the strap-fastening apparatus in a schematic representation.
Figure 7:
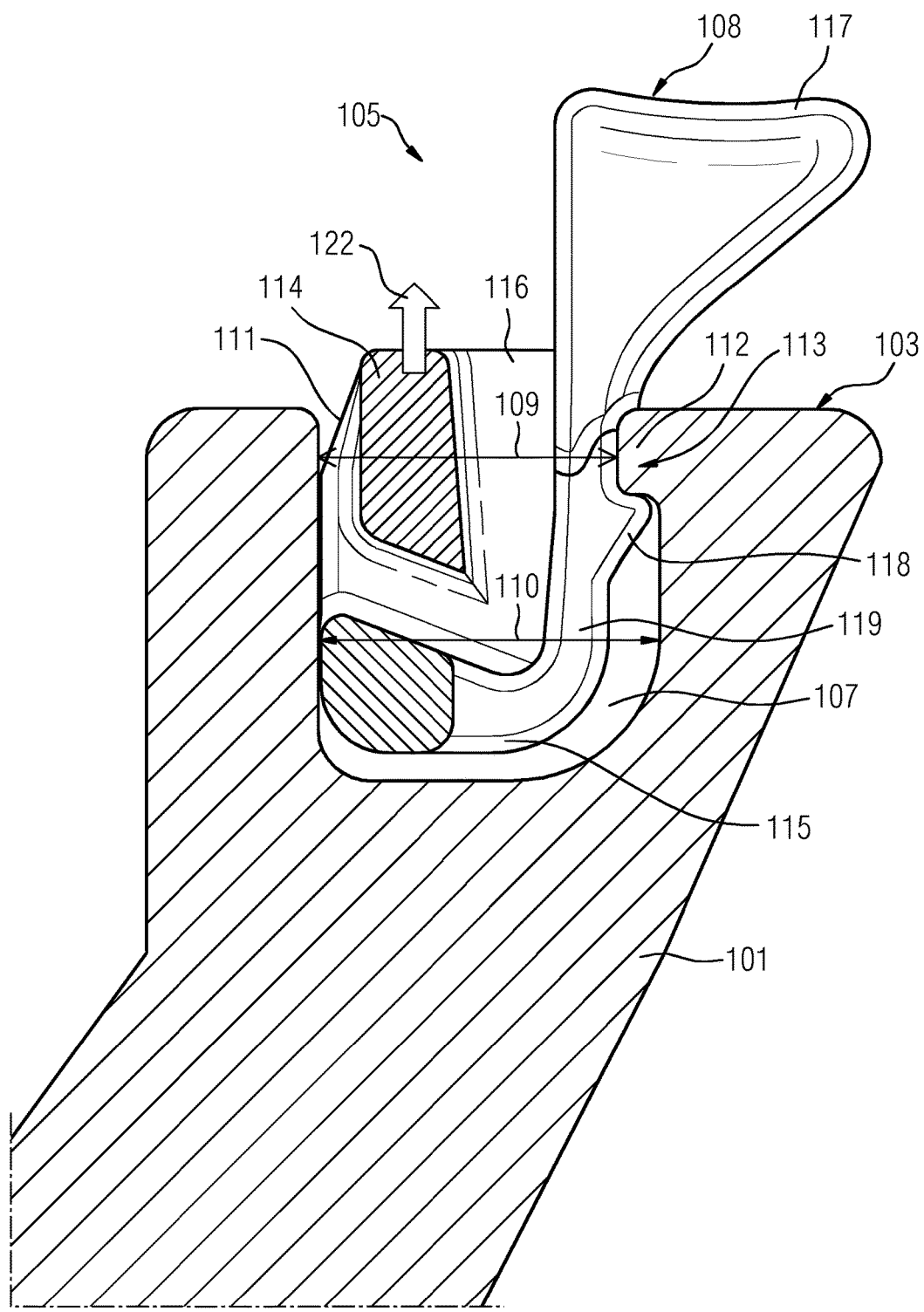
FIG. 7 depicts an example of an effect of a lock force on the fastening clip within the fastening rail in a schematic representation.

A first of the two fastening rails 107 is arranged in a first edge region 103 and a second of the two fastening rails 107 is arranged in a second edge region 103 of the couch 101. The two fastening rails 107 are embodied similarly. Each of the two fastening rails 107 has an opening 109 and a maximum width 110 (FIG. 6). A width of the opening 109 amounts here to at least 60% of the maximum width 110 of the fastening rail 107. The width of the opening 109 may be at least 75% of the maximum width 110 or at least 80% of the maximum width 110 of the fastening rail 107, so that a particularly simple introduction of the fastening clips 108 into the fastening rails 107 is achieved.

The two fastening rails 107 each include a longitudinal extent, wherein the longitudinal extent of the fastening rails 107 is parallel to the longitudinal extent 104 of the couch 101. In the direction of this longitudinal extent of the fastening rails 107, the opening 109 of the fastening rail 107 has a permanently consistent width (FIG. 2).

Furthermore, the two fastening rails 107 each include a web-type rail element 112, wherein the web-type rail elements 112 are arranged in an opening region of the respective fastening rail 107. Each rail of the two fastening rails 107 has just one single web-type rail element 112 here, wherein the web-type rail elements 112 are arranged on in each case just one edge region 113, which runs in the longitudinal extent of the fastening rail 107. The web-type rail elements 112 are arranged here on an edge region 113 of the respective fastening rail 107 facing away from the support region 102 on the respective fastening rail 107, so that the opening region of the fastening rails 107 has a one-sided projection (FIGS. 3, 6, 7, and 8). A concealed region, (e.g., a region concealed by the web-type rail element 112), is present here within the fastening rail 107 only on one side of the fastening rail 107. A second edge region, which likewise runs in the longitudinal extent of the at least one fastening rail 107 and faces the edge region 113 with the web-type rail element 112 within the at least one fastening rail 107, may be formed by a straight continuation of a receiving region of the at least one fastening rail 107.

Figure 4:
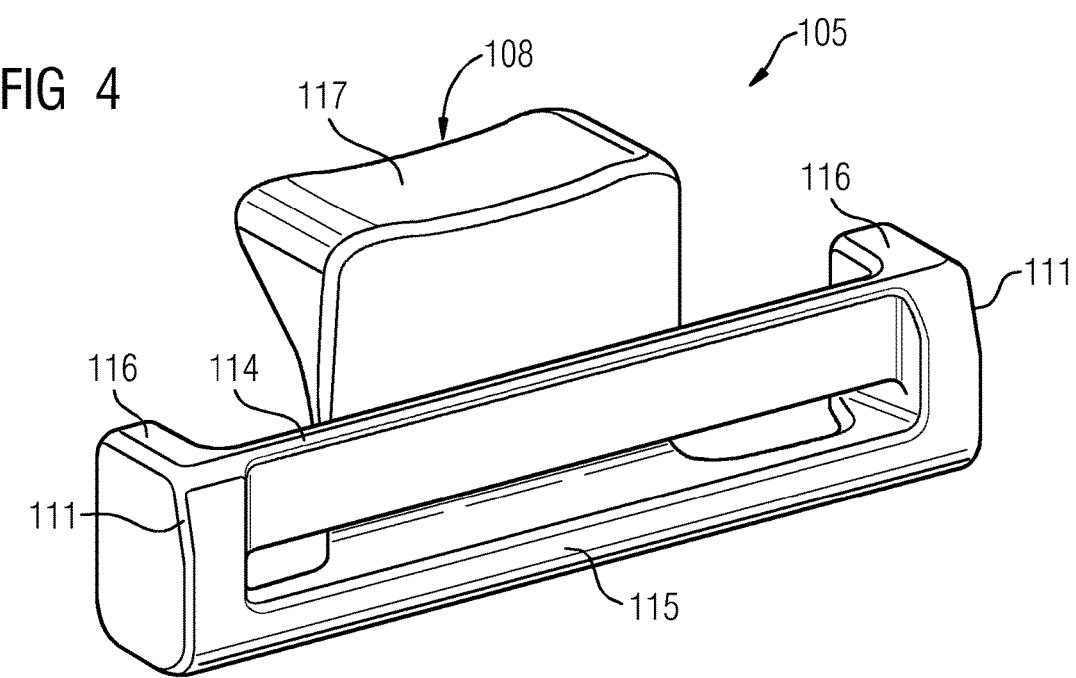
FIG. 4 depicts an example of a fastening clip of the strap-fastening apparatus in a schematic representation.
Figure 5:
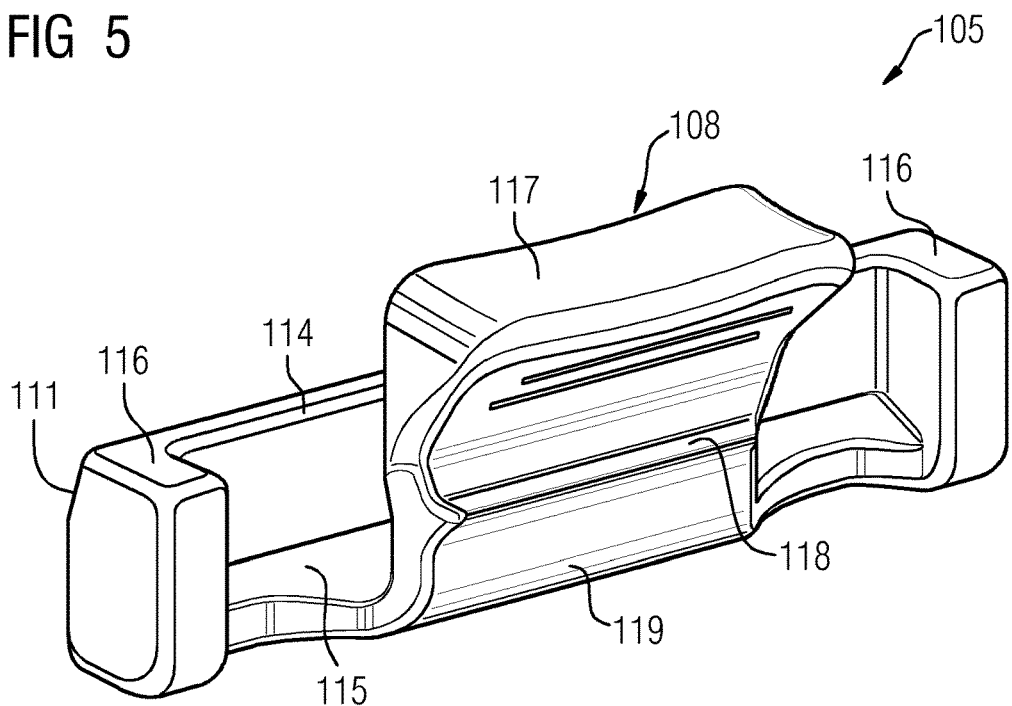
FIG. 5 depicts a further view of the fastening clip of the strap-fastening apparatus in a schematic representation.

The two fastening clips 108 of the strap-fastening apparatus 105 are likewise embodied similarly and each include a strap-fastening element 114. Moreover, the two fastening clips 108 each include a base element 115, on which the strap-fastening element 114 is arranged (FIGS. 4 and 5). The base elements 115 of the two fastening clips 108 are each embodied in a U-shape with two limb elements 116. The strap-fastening element 114 of the fastening clip 108 is arranged in each case between the two limb elements 116 of the U-shaped base element 115. The strap-fastening elements 114 may herewith be arranged with in each case one first edge region on a first of the two limb elements 116 of the respective base element 115 and with a second edge region on a second of the two limb elements 116 of the respective base element 115. The strap-fastening elements 114 may be embodied in the form of a web, so that a safety strap 106 of the strap-fastening apparatus 105 may be guided around the strap-fastening element 114. Moreover, the two strap-fastening elements 114 are arranged on in each case a central region on the limb elements 116, so that the safety strap 106 may be safely guided inside of the fastening clip 108.

The two limb elements 116 of a respective base element 115 have a tapered form 111 on an open side of the base element 115, so that a simple lock of the respective fastening clip 108 may herewith take place with one of the two fastening rails 107.

The fastening clips 108 further include in each case an actuation element 117, a securing element 118, and a connecting web 119 (FIGS. 3, 4, 5, and 7). The actuation elements 117 are configured in each case to actuate, e.g., release the fastening clips 108 from the fastening rail 107 and/or fix the fastening clips 108 within the fastening rails 107, for medical operating staff.

The securing elements 118 are each designed to secure the respective fastening clip 108, within the fastening rail 107, so that the fastening clips 108 are secured against unwanted release and/or falling out of the fastening rail 107. The connecting webs 119 of the fastening clips 108 are provided to connect the actuation elements 117 to the base elements 115 within the fastening clips 108. One of the two securing elements 118 is arranged in each case on one of the connecting webs 119 of the fastening clips 108. The actuation element 117 extends in a direction from the strap-fastening element 114 in the direction of the connecting web 119 away from the connecting web 119.

In a state of the respective fastening clip 108 arranged with one of the two fastening rails 107, the base elements 115 are arranged up to at least 70% within the fastening rail 107. The base elements 115 may be arranged at least 80% within the fastening rail 107 or at least 85% within the fastening rail 107. The base elements 115 are however particularly advantageously arranged at least 90% within the fastening rail 107. The strap-fastening elements 14 are herewith also arranged within the fastening rail 107, wherein the strap-fastening elements 107 are arranged completely within the fastening rail 107. In the state of the respective fastening clip 108 arranged with one of the two fastening rails 107, the respective fastening clip 108 may be arranged moveably within the fastening rail 107, (e.g., moveably along the longitudinal extent of the fastening rail 107), or also be locked with the fastening rail 107.

The actuation element 17 protrudes out of the fastening rail 107 in the state of the respective fastening clip 108 arranged with the fastening rail 107, so that a simple and secure actuation may take place by the medical operating staff. In the state of the fastening clips 108 arranged with one of the two fastening rails 107, these are arranged on the couch 101 such that the actuation element 117 of the respective fastening clip 108 faces the edge region 103 of the couch 101 in a transverse extent of the couch 101 and the strap-fastening element 114 is facing the support region 102. A gripping zone of the actuation element 117 is facing away here from the support region 102 of the patient support apparatus 100 in the state of the respective fastening clip 108 arranged with the fastening rail 107.

In this state of the fastening clips 108 arranged with one of the two fastening rails 107, the fastening clips 108 are arranged within the fastening rails 107 such that the securing element 118 of the respective fastening clip 108 assumes a snap-on connection with the web-type rail element 112 of the fastening rail 107. This snap-on connection secures the fastening clips 108 within the fastening rail 107 from falling out of the fastening rail 107. Moreover, the fastening clips 108 within the fastening rail 107 are moveably supported within the fastening rails 107 in the direction of the longitudinal extent of the fastening rails 107 as long as the fastening clips 108 do not assume a locked state with one of the fastening rails 107. This is particularly advantageous for a precise positioning of the fastening clip 108 for positioning the safety strap 106.

As soon as a tensile force 122 acts on the strap-fastening element 114 due to a tightening of the safety strap 106 by the medical operating staff, this tensile force 122 takes effect such that the fastening clip 108 with the fastening rail 107 locks and is immovably locked with the fastening rail 107 in its position with respect to the direction of the longitudinal extent of the fastening rail 107. This tensile force 122 is depicted in FIG. 2 by an arrow. On account of this tensile force 122, a sub region of the fastening clip 108 that faces the actuation element 117 is moved in the direction of the tensile force 122, which results in a canting of the fastening clip 108 within the fastening rail 107 and thus in a lock.

Figure 8:
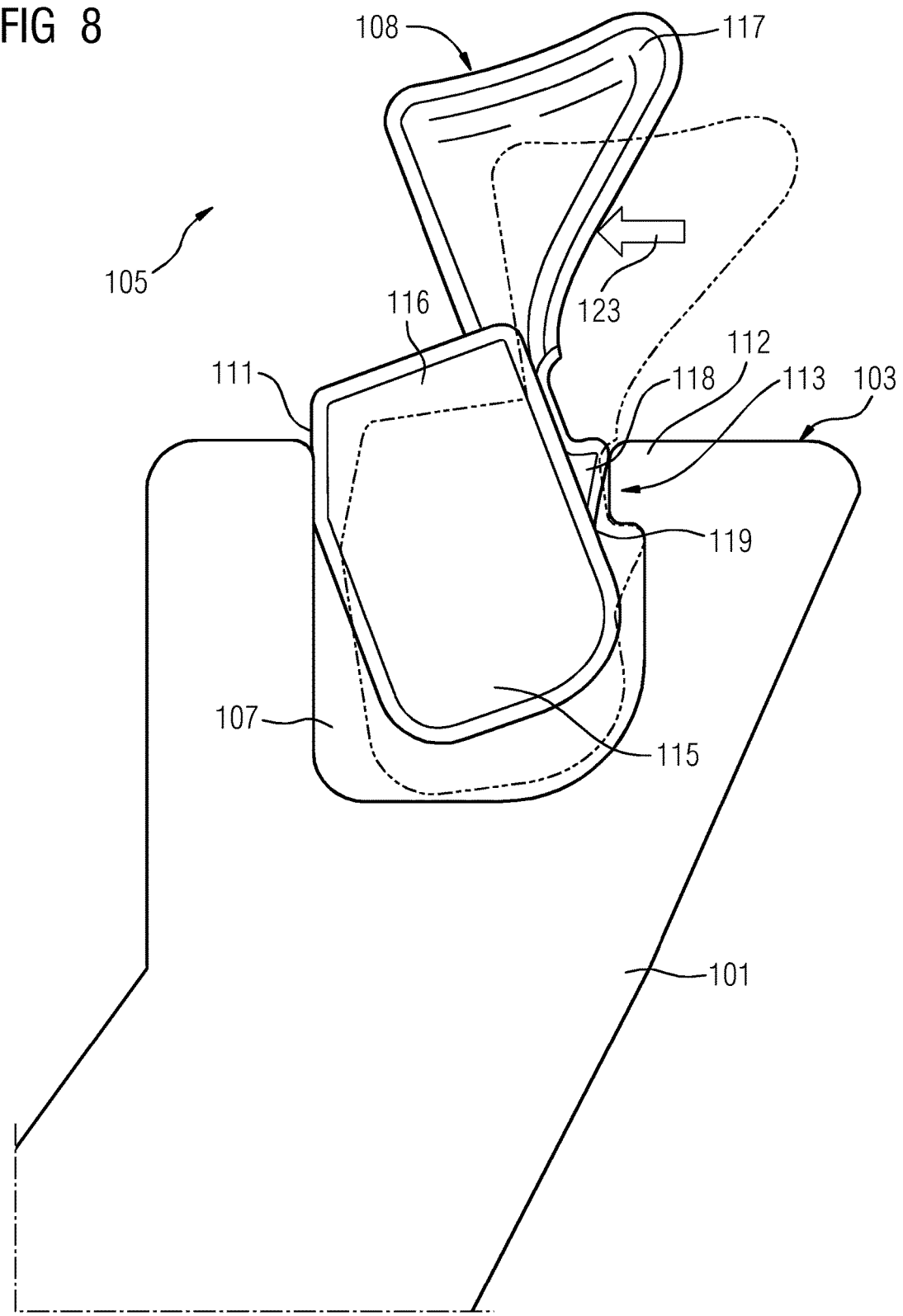
FIG. 8 depicts an example of a release of a lock of the fastening clip with the fastening rail in a schematic representation.

In order to release the lock between the fastening clip 108 and the fastening rail 107, a force 123 is exerted onto the actuation element 108, for instance by the medical operating staff. This force 123 is depicted in FIG. 8 as an arrow and acts in the direction of the transverse extent of the couch 101, e.g., from the edge region 103, in which the fastening rail 107 is arranged, of the couch 101 in the direction of the support region 102. In particular, the force 123 acts from the outside in the direction of a center of the couch 101. A simple achievability of the actuation element 17 for releasing the lock between one of the fastening clips 108 with one of the fastening rails 107 may herewith be achieved for the medical operating personnel.

The strap-fastening apparatus 105, (e.g., the fastening rails 107), is also embodied to be compatible with local magnetic resonance coil apparatuses 120. Local, fixed magnetic resonance coil apparatuses 120 are particularly advantageously arranged within the couch 101 and are used as a support surface for the patient 15. These fixed magnetic resonance coil apparatuses 120 are fixed within the couch 101 by the fastening rail 107. To this end, the local magnetic resonance coil apparatus 120 has fastening elements 121, which are embodied so as to correspond with the fastening rails (FIG. 2).

In an alternative embodiment, the local magnetic resonance coil apparatus 120 may also be formed by a magnetic resonance coil apparatus that may be placed on and/or attached to the patient 15. A magnetic resonance coil apparatus embodied in this way may be embodied so as to be compatible with the strap-fastening apparatus 105, by this magnetic resonance coil apparatus including a fastening clip 108 and/or a fastening rail 107 of the strap-fastening apparatus 105.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A strap-fastening apparatus for fastening safety straps, the strap-fastening apparatus comprising:
    a fastening rail having an opening and a maximum width, as measured in a direction of a longitudinal extent of the fastening rail, wherein a width of the opening is less than the maximum width; and
    a fastening clip having a strap-fastening element, a securing element, an actuation element, and a connecting web, wherein the securing element is positioned on the connecting web,
    wherein the strap-fastening element and the securing element are configured to be arranged within the fastening rail and the actuation element is configured to be arranged outside of the fastening rail in a first position of the fastening clip,
    wherein a width of the fastening clip as measured in the direction of the longitudinal extent, in the first position, is greater than the width of the opening of the fastening rail such that the fastening clip is configured to be secured within the fastening rail in the first position,
    wherein the actuation element is configured to move in the direction of the longitudinal extent by a force exerted on the actuation element,
    wherein the connecting web is configured to deform to release the securing element from within the fastening rail, therein defining a second position of the fastening clip, and
    wherein the fastening clip is configured to be removed from the fastening rail in the second position.

2. The strap-fastening apparatus as claimed in claim 1, wherein the fastening clip further comprises a base element on which the strap-fastening element is arranged.

3. The strap-fastening apparatus as claimed in claim 2, wherein the base element, in the state of the fastening clip arranged with the fastening rail, is arranged at least 70% within the fastening rail.

4. The strap-fastening apparatus as claimed in claim 2, wherein the base element is embodied in a U-shape with two limb elements and the strap-fastening element is arranged between the two limb elements.

5. The strap-fastening apparatus as claimed in claim 4, wherein the connecting web connects the actuation element to the base element.

6. The strap-fastening apparatus as claimed in claim 1, wherein the fastening clip further comprises a base element on which the strap-fastening element is arranged, and
wherein the connecting web connects the actuation element to the base element.

7. The strap-fastening apparatus as claimed in claim 1, wherein, in order to release a lock between the fastening clip and the fastening rail, the force to the longitudinal extent of the fastening rail acts on the fastening clip.

8. The strap-fastening apparatus as claimed in claim 1, wherein the fastening clip locks with the fastening rail upon an effect of a tensile force on the strap-fastening element.

9. The strap-fastening apparatus as claimed in claim 1, wherein the fastening clip comprises a snap-on connection with the fastening rail.

10. The strap-fastening apparatus as claimed in claim 1, wherein the width of the opening is at least 60% of the maximum width.

11. The strap-fastening apparatus as claimed in claim 10, wherein, in the direction of the longitudinal extent, the opening has a uniform width.

12. The strap-fastening apparatus as claimed in claim 10, wherein the fastening rail comprises a rail element in a form of a web,
wherein the rail element is arranged in the opening of the fastening rail, and
wherein the rail element is only arranged on an edge region running in a direction of the longitudinal extent of the fastening rail.

13. A patient support apparatus comprising:
a strap-fastening apparatus comprising:
a fastening rail having an opening and a maximum width, as measured in a direction of a longitudinal extent of the fastening rail, wherein a width of the opening is less than the maximum width; and
fastening clip having a strap-fastening element, a securing element, an actuation element, and a connecting web, wherein the securing element is positioned on the connecting web,
wherein the strap-fastening element and the securing element are configured to be arranged within the fastening rail and the actuation element is configured to be arranged outside of the fastening rail in a first position of the fastening clip,
wherein a width of the fastening clip as measured in the direction of the longitudinal extent, in the first position, is greater than the width of the opening of the fastening rail such that the fastening clip is configured to be secured within the fastening rail in the first position,
wherein the actuation element is configured to move in the direction of the longitudinal extent by a force exerted on the actuation element,
wherein the connecting web is configured to deform to release the securing element from within the fastening rail, therein defining a second position of the fastening clip, and
wherein the fastening clip is configured to be removed from the fastening rail in the second position.

14. The patient support apparatus as claimed in claim 13, further comprising:
a couch,
wherein the couch includes the fastening rail and the fastening rail arranged in an edge region of the couch that extends along a longitudinal extent of the couch.

15. The patient support apparatus as claimed in claim 14, wherein, in order to release a lock between the fastening clip and the fastening rail, a force at right angles to the longitudinal extent of the fastening rail acts inwards on the fastening clip directed from the edge region of the couch.

16. The patient support apparatus as claimed in claim 13, wherein the strap-fastening apparatus is compatible with a local magnetic resonance coil apparatus.

17. A medical imaging apparatus comprising:
a patient support apparatus comprising:
a strap-fastening apparatus having:
a fastening rail having an opening and a maximum width, as measured in a direction of a longitudinal extent of the fastening rail, wherein a width of the opening is less than the maximum width; and
a fastening clip having a strap-fastening element, a securing element, an actuation element, and a connecting web, wherein the securing element is positioned on the connecting web,
wherein the strap-fastening element and the securing element are configured to be arranged within the fastening rail and the actuation element is configured to be arranged outside of the fastening rail in a first position of the fastening clip,
wherein a width of the fastening clip as measured in the direction of the longitudinal extent, in the first position, is greater than the width of the opening of the fastening rail such that the fastening clip is configured to be secured within the fastening rail in the first position,
wherein the actuation element is configured to move in the direction of the longitudinal extent by a force exerted on the actuation element,
wherein the connecting web is configured to deform to release the securing element from within the fastening rail, therein defining a second position of the fastening clip, and
wherein the fastening clip is configured to be removed from the fastening rail in the second position; and
a couch, wherein the couch includes the fastening rail and the fastening rail arranged in an edge region of the couch that extends along a longitudinal extent of the couch; and
a local magnetic resonance coil,
wherein the strap-fastening apparatus is compatible with the local magnetic resonance coil.

* * * * *